United States Patent
Wang (10) Patent No.: US 12,186,400 B2
(45) Date of Patent: Jan. 7, 2025

(54) MICROMOLECULAR COMPOUND SPECIFICALLY DEGRADING TAU PROTEIN, AND APPLICATION THEREOF

(71) Applicant: Shanghai Qiangrui Biotech Co., Ltd., Shanghai (CN)

(72) Inventor: Yipeng Wang, Shanghai (CN)

(73) Assignee: Yipeng Wang, Shanghai (CN)

( * ) Notice: Subject to any disclaimer, the term of this patent is extended or adjusted under 35 U.S.C. 154(b) by 854 days.

(21) Appl. No.: 17/292,677

(22) PCT Filed: Nov. 9, 2018

(86) PCT No.: PCT/CN2018/114838
§ 371 (c)(1),
(2) Date: May 10, 2021

(87) PCT Pub. No.: WO2020/093370
PCT Pub. Date: May 14, 2020

(65) Prior Publication Data
US 2022/0001017 A1    Jan. 6, 2022

(51) Int. Cl.
*A61K 47/55* (2017.01)
*A61P 25/08* (2006.01)
(Continued)

(52) U.S. Cl.
CPC ............. *A61K 47/55* (2017.08); *A61P 25/08* (2018.01); *A61P 25/16* (2018.01); *A61P 25/28* (2018.01)

(58) Field of Classification Search
CPC .......... A61K 47/55; A61P 25/28; A61P 25/08; A61P 25/16
See application file for complete search history.

(56) References Cited

U.S. PATENT DOCUMENTS

| | | |
|---|---|---|
| 2014/0356322 A1 | 12/2014 | Crews et al. |
| 2018/0125821 A1 | 5/2018 | Crew et al. |

FOREIGN PATENT DOCUMENTS

| | | |
|---|---|---|
| CN | 104736569 A | 6/2015 |
| CN | 105801708 A | 7/2016 |

(Continued)

OTHER PUBLICATIONS

Cummings et al. Alzheimer's Research & Therapy (2023) 15:168 (Year: 2023).*

(Continued)

*Primary Examiner* — Clinton A Brooks
*Assistant Examiner* — Jerica Katlynn Wilson
(74) *Attorney, Agent, or Firm* — Calfee, Halter & Griswold LLP (57) ABSTRACT

The present disclosure discloses a micromolecular compound specifically degrading tau protein, and an application thereof. The chemical structure of the micromolecular compound specifically degrading tau protein is TBM-L-ULM or a pharmaceutically acceptable salt, enantiomer, stereoisomer, solvate, polymorph or N-oxide thereof, TBM being a tau protein-binding moiety, L being a linking group, and ULM being a ubiquitin ligase-binding moiety, the tau protein-binding moiety and the ubiquitin ligase-binding moiety being connected by means of the linking group. The micromolecular compound specifically degrading tau protein may increase tau protein degradation in a cell, thereby decreasing tau protein content.

10 Claims, 2 Drawing Sheets

(51) Int. Cl.
*A61P 25/16* (2006.01)
*A61P 25/28* (2006.01)

(56) References Cited

FOREIGN PATENT DOCUMENTS

| | | |
|---|---|---|
| CN | 108601764 A | 9/2018 |
| EP | 1229025 A1 | 8/2002 |
| WO | 2017185023 A1 | 10/2017 |
| WO | 2017185034 A1 | 10/2017 |
| WO | WO-2018102067 A2 * 6/2018 ........... A61K 31/381 |

OTHER PUBLICATIONS

Schafer et al. Drug Discovery Today 2008, 13 (21/22), 913-916. (Year: 2000).*
Horig et al. Journal of Translational Medicine 2004, 2(44) (Year: 2004).*
English Translation of International Search Report from PCT/CN2018/114838 dated Jul. 25, 2019 (5 pages).

* cited by examiner

MICROMOLECULAR COMPOUND SPECIFICALLY DEGRADING TAU PROTEIN, AND APPLICATION THEREOF

CROSS-REFERENCE TO RELATED APPLICATIONS

This application is a 371 of PCT Application No. PCT/CN2018/114838 filed on Nov. 9, 2018, the contents of which are hereby incorporated by reference as if recited in their entirety.

FIELD

The present disclosure relates to the technical field of bifunctional molecular compounds, and in particular to a micromolecular compound (named "JT01" hereinafter) specifically degrading tau protein and an application thereof.

BACKGROUND

Alzheimer's Disease (AD) is the most common form of dementia, accounting for about 50-70% of dementia. The statistics indicate that there are about 10 million AD patients in China and 44 million AD patients worldwide in 2016. The incidence rate of AD will further rise along with the aging process of the population, it is expected that there will be about 40 million AD patients in China by 2050. All the medicaments for the treatment of AD at present are Symptomatic drugs, which can only provide short-term relief of symptoms and do not slow the progression of the illness. Disease-modifying drugs that substantially modify the progression of AD are urgently expected worldwide.

Two characteristic pathological changes of AD are Senile Plaques (SPs) and Neurofibrillary tangles (NFTs), which are polymers formed from β-amyloid (Aβ) and hyperphosphorylated tau protein, respectively, in which the tau lesions, instead of the Aβ lesions, is positively correlated with the dementia degree of AD. Recent studies have shown that Aβ-induced neurotoxicity is mediated by tau, tau is necessary for Aβ-induced neurotoxicity. Tau is a Prion-like protein that can propagate between neurons to cause spread of the tauopathy. Taken together, it suggests that tau may be an essential drug target for AD.

Besides AD, tau aggregation is also seen in a range of neurodegenerative diseases such as frontotemporal dementia linked to chromosome-17 with Parkinsonism (FTDP-17), Pick's Disease (PiD), progressive supranuclear palsy (PSP), corticobasal degeneration (CBD), primary age-related tauopathy (PART), argyrophilic grain disease (AGD), aging-related tau astrogliopathy (ARTAG), chronic traumatic encephalopathy (CTE), Global glial tauopathy (GGT), Parkinson's disease (PD), Huntington's Disease (HD). Such diseases including AD am collectively referred to as tauopathies. Tau protein is a significant contributor to this kind of diseases, thus it is also an important therapeutic target for this kind of disease.

Although there are a number of tau-based therapeutic approaches at present, one of the most attractive solutions is to reduce the content of the intracellular tau protein. The solution is preferred mainly based on the following reasons: (1) it is demonstrated by many evidences that reducing the content of tau protein rarely causes side effect in the animal models; (2) reducing the content of tau protein may inhibit aggregation of tau protein, which is an important cause of neurodegeneration; and (3) reducing the content of tau protein can reduce the effects of neuronal excitotoxicity resulting from a variety of factors (e.g., Aβ). Therefore, reducing the content of tau protein is also regarded as a novel and potential scheme for treating epilepsy and stroke.

There are two common technical methods used for reducing the intracellular target proteins: (1) suppressing the expression of the target protein using siRNA, miRNA, or antisense oligonucleotides. Because the oligonucleotides have undesirable distribution in tissues, poor pharmacokinetics, and probably-off-target effects, the clinical applications of said oligonucleotides are currently restrained, and such a method needs further improvement. (2) Enhancing the degradation of target protein. The common methods used to enhance the degradation of target protein are to promote the activity of the protein degradation systems including the protease system and the autophagy system. However, non-specifically enhancing activity of the protein degradation systems is prone to cause severe side effects resulting from degradation of other non-target proteins, as a result, there is not any drug that activates the protein degradation system has been approved for clinical use at present. The ideal method would be only selectively enhancing degradation of the target protein while avoiding degradation of the non-target protein due to the enhanced activity of the protein degradation system.

SUMMARY

The present disclosure aims to construct a micromolecular compound specifically for degrading tau protein. To achieve this, the inventor of the present disclosure has performed in-depth research and discovered that the PROteolysis TArgeting Chimeras (PROTAC) technology can be used for the construction of a bifunctional molecular compound composed of one moiety specifically binding target protein and another moiety binding a specific ubiquitin ligase, the two are connected via a linker. The compound constructed in such a manner can simultaneously couple with the target protein and the ubiquitin ligase, and thereby brings the target protein into proximity with the ubiquitin ligase, enabling the ubiquitination and subsequent degradation of the target protein by the proteasome. Furthermore, the PROTAC technology has the following advantages in addition to selectivity for the target protein: (1) it is effective for many targets which are traditionally regarded as undruggable for many conventional medicaments. Many traditional micromolecular drugs can only play an inhibitive role by acting on the specific binding pockets of the target protein. The PROTAC technology does not have such a limitation, as long as it interacts with any segment of the target protein and does not require high affinity, which results in rapid degradation of the target protein and thereby inhibits the function of the target protein. (2) The PROTAC technology can be used repeatedly inside the cells and may produce an effect similar to the catalytic effect, thus it is therapeutically effective without requiring a high concentration.

To this end, the present disclosure provides a micromolecular compound (i.e., JT01) that specifically degrades tau protein, wherein the chemical structure of the compound is TBM-L-ULM, or a pharmaceutically acceptable salt, enantiomer, stereoisomer, solvate, polymorph, or N-oxide thereof, wherein TBM is a tau protein-binding moiety, L is a linker group, and ULM is a ubiquitin ligase-binding moiety, the tau protein-binding moiety is connected with the ubiquitin ligase-binding moiety via the linker group.

In a preferred embodiment, the ULM is capable of binding with E3 ubiquitin ligase.

Further preferably, the E3 ubiquitin ligase is VHL E3 ubiquitin ligase or CRBN E3 ubiquitin ligase.

In a preferred embodiment, the ULM is a group having a structure represented by Formula (1), Formula (1)

Wherein $R^1$ is a hydroxyl, or a group which is metabolized to hydroxyl in the body of a patient or a subject;

$R^2$ is -NH—$R^4$—Ar-HET, wherein $R^4$ is a C1-C3 alkylene, Ar is a C6-C12 arylene, and HET is an optionally substituted thiazole or isothiazole;

$R^3$ is —$CHR^5$-M-, the ULM is connected with the linker group L via M, wherein $R^5$ is a C1-C4 alkyl, M is a bond, a C1-C4 alkylene, —NH— or —NH—C(O)—$R^6$—, wherein $R^6$ is a C1-C4 alkylene.

In a preferred embodiment, L is the group —X—Y—Z—, X is linked to TBM, and Z is linked to ULM, wherein X is a bond, C1-C4 alkylene, —NH— or —NH—C(O)—$R^7$—, wherein $R^7$ is a bond or a C1-C4 alkylene;

Y is —$R^8$—($R^{10}$-E—$R^{11}$)$_n$—$R^9$—, wherein $R^8$ and $R^9$ each is a bond or a C1-C8 alkylene, $R^{10}$ and $R^{11}$ each is a C1-C4 alkylene, n is an integer of 0-10, E is O, S, an amide group, a piperazinyl group, $NR^{12}$, S(O), S(O)2, —S(O)2O, —OS(O)2, OS(O)2O, or -continued wherein $E^1$ is O, S, $CHR^{12}$ or $NR^{12}$, $R^{12}$ is H or a C1-C3 alkyl optionally substituted with one or two hydroxyl groups;

Z is -A—B—, wherein A is a bond, O, or S; B is a bond, a C1-C4 alkylene, or —$R^{13}$—C(O)—, wherein $R^{13}$ is a C1-C4 alkylene.

In a preferred embodiment, the TBM is a group having the structure expressed by Formula (2), or a group further modified by a substituent at the sites ①, ②, ③, ④, ⑤, ⑥, ⑦, ⑧, ⑨ or ⑩ of a group having the structure expressed by Formula (2), wherein TBM is connected with the linker group L through sites ①, ②, ③, ④, ⑤, ⑥, ⑦, ⑧, ⑨ or ⑩ of Formula (2), Formula (2)

Wherein $R^{14}$ is a C1-C4 alkylene, $R^{15}$ and $R^{16}$ each is a C1-C4 alkyl, $R^{17}$ is a bond, H, a C1-C4 alkyl, or —$R^{18}$—C(O)—, wherein $R^{18}$ is a C1-C4 alkylene.

In a preferred embodiment, the micromolecular compound specifically degrading a tau protein has the following structural formula:

The present disclosure further provides a method for degrading tau protein in a patient body in need, the method comprises administering the patient with an effective amount of the aforementioned micromolecular compound.

In a preferred embodiment, the micromolecular compound is administered to the patient by at least one mode selected from the group consisting of: nasal, inhalation, topical, oral, intramuscular, subcutaneous, transdermal, peritoneal, epidural, intrathecal, and intravenous routes.

The present disclosure also provides an application of the aforementioned micromolecular compound for preparing a medicament for treatment or prevention of a disease associated with the tau protein.

Optionally, the disease is at least one selected from the group consisting of Alzheimer's disease (AD), frontotemporal dementia linked to chromosome-17 parkinsonism (FTDP-17), Pick's disease (PiD), progressive supranuclear palsy (PSP), corticobasal degeneration (CBD), primary age-related tauopathy (PART), argyrophilic grain disease (AGD), aging-related tau astrogliopathy (ARTAG), chronic traumatic encephalopathy (CTE), globular glial tauopathy (GGT), Parkinson's disease (PD), Huntington's disease (HD), cerebral stroke and epilepsy.

It is demonstrated through the immunoblot test that the micromolecular compound specifically degrading tau protein of the present disclosure can enhance degradation of the tau protein in cells, thereby reducing the content of tau protein. Thus it indicates that the micromolecular compound specifically degrading tau protein of the present disclosure can play its role in the prevention and treatment of a range of tauopathies including Alzheimer's disease.

DETAILED DESCRIPTION

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values, and the individual point value of the various ranges, and the individual point values may be combined to produce one or more new numerical ranges, which should be deemed to have been specifically disclosed herein.

The chemical structure of the micromolecular compound specifically degrading tau protein of the present disclosure is TBM-L-ULM, or a pharmaceutically acceptable salt, enantiomer, stereoisomer, solvate, polymorph, or N-oxide thereof, wherein TBM is a tau protein-binding moiety, L is a linker group, and ULM is a ubiquitin ligase-binding moiety, the tau protein-binding moiety is connected with the ubiquitin ligase-binding moiety via the linker group.

Preferably, the ULM is capable of binding with E3 ubiquitin ligase. Preferably, the E3 ubiquitin ligase is VHL E3 ubiquitin ligase or CRBN E3 ubiquitin ligase.

In a preferred embodiment, the ULM is a group having a structure represented by Formula (1), Formula (1)

Wherein $R^1$ is a hydroxyl, or a group which is metabolized to hydroxyl in the body of a patient or a subject;

$R^2$ is —NH—$R^4$—Ar-HET, wherein $R^4$ is a C1-C3 alkylene (such as methylene, ethylidene, or propylidene), Ar is a C6-C12 arylene (e.g., phenyl or naphthyl), and HET is an optionally substituted thiazole or isothiazole;

$R^3$ is —CHR$^5$-M-, the ULM is connected with the linker group L via M, wherein $R^5$ is a C1-C4 alkyl (e.g. methyl, ethyl, propyl or butyl), M is a bond, a C1-C4 alkylene (e.g., methylene, ethylidene, propylidene or butylidene), —NH— or —NH—C(O)—$R^6$—, wherein $R^6$ is a C1-C4 alkylene (e.g., methylene, ethylidene, propylidene or butylidene); wherein the ULM is coupled with the linker group L via "-M-". "R6—" is directly connected with the linker group L when "-M-" is —NH—C(O)—$R^6$—.

Further preferably, in the structure shown in Formula (1), $R^1$ is hydroxyl; R2 is —NH—$R^4$—Ar-HET, wherein $R^4$ is methylene and Ar is phenyl; $R^3$ is —CHR$^5$—NH— or —CHR$^5$—NH—C(O)—$R^6$—, wherein $R^5$ is —C(CH$_3$)$_3$ and $R^6$ is methylene.

In a more preferred embodiment, L is the group —X—Y—Z—, X is linked to TBM, and Z is linked to ULM, wherein X is a bond, C1-C4 alkylene (e.g., methylene, ethylidene, propylidene or butylidene), —NH— or —NH—C(O)—$R^7$—, wherein $R^7$ is a bond or a C1-C4 alkylene (e.g., methylene, ethylidene, propylidene or butylidene);

Y is —$R^8$—($R^{10}$-E-$R^{11}$)$_n$—$R^9$—, wherein $R^8$ and $R^9$ each is a bond or a C1-C8 alkylene (e.g., methylene, ethylidene, propylidene, butylidene, pentylidene, hexylidene, heptylidene, or octylidene), $R^{10}$ and $R^{11}$ each is a C1-C4 alkylene (e.g., methylene, ethylidene, propylidene or butylidene), n is an integer of 0-10 (e.g., 0, 1, 2, 3, 4, 5, 6, 7, 8, 9, or 10), E is O, S, an amide group, a piperazinyl group, NR$^{12}$, S(O), S(O)$_2$, —S(O)$_2$O, —OS(O)$_2$, OS(O)$_2$O, wherein $E^1$ is O, S, CHR$^{12}$ or NR$^{12}$, $R^{12}$ is H or a C1-C3 alkyl optionally substituted with one or two hydroxyl groups;

Z is -A-B—, wherein A is a bond, O, or S; B is a bond, a C1-C4 alkylene (e.g., methylene, ethylidene, propylidene or butylidene), or —R³—C(O)—, wherein R¹³ is a C1-C4 alkylene (e.g., methylene, ethylidene, propylidene or butylidene).

In a more preferred embodiment, the TBM is a group having the structure expressed by Formula (2), or a group further modified by a substituent at the sites ①, ②, ③, ④, ⑤, ⑥, ⑦, ⑧, ⑨ or ⑩ of a group having the structure expressed by Formula (2), wherein TBM is connected with the linker group L through sites ①, ②, ③, ④, ⑤, ⑥, ⑦, ⑧, ⑨ or ⑩ of Formula (2), Formula (2)

Wherein R¹⁴ is a C1-C4 alkylene (e.g., methylene, ethylidene, propylidene or butylidene), R¹⁵ and R¹⁶ each is a C1-C4 alkyl (e.g., methyl, ethyl, propyl, or butyl), R¹⁷ is a bond, H, a C1-C4 alkyl(e.g., methyl, ethyl, propyl, or butyl), or —R¹⁸—C(O)—, wherein R¹⁸ is a C1-C4 alkylene (e.g., methylene, ethylidene, propylidene or butylidene).

Wherein, the substituent at the sites ①, ②, ③, ④, ⑤, ⑥, ⑦, ⑧, ⑨ or ⑩ of a group having the structure expressed by the modification Formula (2) may be a halogen (e.g. fluorine or chlorine), C1-C4 alkyl (e.g. methyl, ethyl, propyl or butyl), C1-C4 alkoxy group (e.g. methoxyl, ethoxyl, propoxyl or butoxyl), carboxyl, amino, amine, C6-C18 aryl (e.g. phenyl) or benzyl group.

Further preferably, in the structure expressed by the Formula (2), the TBM is connected with the linker group L through a site ⑤ in the Formula (2), R¹⁴ is ethylene, R¹⁵ and R¹⁶ each is methyl, and R¹⁷ is a bond, methylene or —CH₂—C(O)—.

In the most preferred embodiment, the micromolecular compound specifically degrading a tau protein has the following structural formula:

The micromolecular compound specifically degrading a tau protein can be prepared according to the following process route:

Compound4

The specific preparation process comprises the following steps:

(1) Preparation of Compound B

The compound A was dissolved in N, N-Dimethylacetamide (DMA), and then the potassium acetate (KOAc), 4-methylthiazole, and lead acetate (Pd(AcO)$_2$) were added under the protection of nitrogen gas (N$_2$). The suspension was degassed under vacuum and replaced with hydrogen gas. The suspension was subsequently subjected to stirring, heating, and refluxing overnight under the atmosphere of nitrogen gas (N$_2$). After the reaction was complete, the reaction solution was filtered, the filtrate was concentrated to dryness, and then purified by a silica gel column to obtain a compound B (a yellow oily substance).

(2) Preparation of Compound C

The compound B was dissolved in methyl alcohol (MeOH, or methanol) and NH₄OH, and the Raney Nickel (Reney Ni) was then added under the protection of nitrogen gas (N₂). The suspension was degassed under vacuum and replaced with hydrogen gas. The reaction suspension was subsequently stirred overnight at room temperature under an atmosphere of hydrogen gas. After the reaction was complete, the reaction solution was filtered, the filtrate was concentrated to dryness, and then purified by silica gel column to yield a compound C (a pale yellow oily substance).

(3) Preparation of Compound D

The compound C was dissolved in N, N-Dimethylformamide (DMF); the N, N-Diisopropylethylamine (DIPEA), and Boc-(2S, 4R)-4-hydroxy-2-pyrrolidine carboxylic acid were added under the protection of nitrogen gas (N₂). 2-(7-benzotriazole oxide-N, N, N', N'-tetramethylurea hexafluorophosphate (HATU) was subsequently added after the reaction solution was cooled to a temperature of 0~5° C. The reaction solution was stirred overnight at room temperature under the protection of nitrogen gas. After the reaction was complete, the reaction mixture was poured into iced water, and extracted with ethyl acetate (EA), and the organic phases were washed with salt solution. The organic phases were combined, and subsequently dried and concentrated with anhydrous sodium sulfate, and then purified by silica gel column to obtain a compound D.

(4) Preparation of Compound E

The compound D was dissolved in dichloromethane (DCM), and trifluoroacetic acid (TFA) was added. The reaction solution was stirred at room temperature to carry out the reaction. After the reaction was complete, the reaction product was subjected to concentration to obtain a compound E.

(5) Preparation of Compound 4-7

The compound E was dissolved in DMF, the DIPEA and N-Boc-L-tert-leucine were added under the protection of nitrogen gas (N₂). HATU was subsequently added after the reaction solution was cooled to a temperature of 0~5° C. The reaction solution was stirred overnight at room temperature under the protection of nitrogen gas. After the reaction was complete, the reaction mixture was poured into iced water, and extracted with ethyl acetate (EA), and the organic phases were washed with salt solution. The organic phases were combined, and subsequently dried and concentrated with anhydrous sodium sulfate, and then purified by silica gel column to obtain a compound 4-7.

(6) Preparation of Compound 4-8

The compound 4-7 was dissolved in DCM, and TFA was then added. The reaction solution was stirred at room temperature. After the reaction was complete, the reaction product was concentrated to obtain a compound 4-8.

(7) Preparation of Compound 4-9

The compound 4-8 was dissolved in DMF; DIPEA, and 2,2-dimethyl-4-oxo-3,8,11,14-tetraoxa-5-azahexadecane-16-oleic acid were added under the protection of nitrogen gas (N₂). HATU was then added after the reaction solution was cooled to a temperature of 0~5° C. The reaction solution was then stirred overnight at room temperature under the protection of nitrogen gas. After the reaction was complete, the reaction mixture was poured into iced water, and extracted with EA, and the organic phases were washed with salt solution. The organic phases were combined, and subsequently dried, and concentrated with anhydrous sodium sulfate, and then purified with a silica gel column to obtain a compound 4-9.

(8) Preparation of Compound 4-10

The compound 4-9 was dissolved in DCM, and then EA/HC was added. The reaction solution was stirred at room temperature. After the reaction was complete, the reaction product was subjected to concentration to obtain a compound 4-10.

(9) Preparation of Compound 4-12

The compound 3-3 and the sarcosine were dissolved in DMF, and triethylamine (TEA) was added. The reaction solution was then stirred overnight under the protection of nitrogen gas (N₂). After completion of the reaction, the reaction mixture was poured into iced water, and extracted with EA, the organic phases were washed with salt solution. The organic phases were combined, and subsequently dried and concentrated with anhydrous sodium sulfate. The crude product was purified by silica gel chromatography to obtain a compound 4-12.

(10) Preparation of Compound 4 (Target Compound)

The compound 4-12 was dissolved in DMF, the DIPEA and the compound 4-10 were added under the protection of nitrogen gas (N₂). HATU was then added after the reaction solution was cooled to a temperature of 0~5° C. The reaction solution was then stirred overnight at room temperature under the protection of nitrogen gas. After the reaction was complete, the reaction mixture was poured into iced water, and extracted with EA, and the organic phases were washed with salt solution. The organic phases were combined, and subsequently dried, and concentrated with anhydrous sodium sulfate, and then purified with a silica gel column to produce a compound 4 (a hygroscopic white foamy solid).

The present disclosure further provides a method for degrading tau protein in a patient body in need, the method comprises administering the patient with an effective amount of the compound provided by the present disclosure.

In the above method, the compound can be administered to the patient by at least one mode selected from the group consisting of: nasal, inhalation, topical, oral, intramuscular, subcutaneous, transdermal, peritoneal, epidural, intrathecal, and intravenous routes.

The present disclosure also provides an application of the compound for preparing a medicament for the treatment or prevention of a disease associated with tau protein. The disease may be at least one selected from the group consisting of Alzheimer's disease (AD), frontotemporal dementia linked to chromosome-17 parkinsonism (FTDP-17), Pick's disease (PiD), progressive supranuclear palsy (PSP), corticobasal degeneration (CBD), primary age-related tauopathy (PART), argyrophilic grain disease (AGD), aging-related tau astrogliopathy (ARTAG), chronic traumatic encephalopathy (CTE), globular glial tauopathy (GGT), Parkinson's disease (PD), Huntington's disease (HD), cerebral stroke and epilepsy.

The present disclosure will be described below in detail with reference to examples.

EXAMPLES (1) Preparation of Compound B

The compound A (1.82 g, 10 mmol) was dissolved in 25 mL of DMA, and then the KOAc (1.98 g, 20 mmol), 4-methylthiazole (1.5 g, 15 mmol) and Pd(AcO)₂ (220 mg, 1 mmol) were added under protection of nitrogen gas (N₂). The suspension was degassed under vacuum and replaced with hydrogen gas for three times. The suspension was subsequently subjected to stirring, heating, and refluxing overnight under the atmosphere of nitrogen gas. The completion of reaction was confirmed by means of the Thin Layer Chromatography (TLC). The reaction solution was filtered, the filtrate was concentrated to dryness, and then purified by a silica gel column to obtain 1.5 g of compound B, which was a yellow oily substance.

(2) Preparation of Compound C

The compound B (300 mg, 1.498 mmol) was dissolved in 10 mL MeOH and 1 mL NH$_4$OH, and 200 mg Raney Nickel (Reney Ni) was then added under the protection of nitrogen gas (N$_2$). The suspension was degassed under vacuum and replaced with hydrogen gas for three times. The reaction suspension was subsequently stirred overnight at room temperature under an atmosphere of hydrogen gas. The completion of reaction was confirmed by means of the TLC (DCM/EA=1:1). The reaction solution was filtered, the filtrate was concentrated to dryness, and then purified by a silica gel column to obtain 110 mg of compound C, which was a pale yellow oily substance.

(3) Preparation of Compound D

The compound C (110 mg, 0.538 mmol) was dissolved in 3 mL of DMF; the DIPEA (200 mg, 1.547 mmol) and Boc-(2S,4R)-4-hydroxy-2-pyrrolidine carboxylic acid (131 mg, 0.566 mmol) were added under the protection of nitrogen gas (N$_2$). HATU (245 mg, 0.644 mmol) was subsequently added after the reaction solution was cooled to a temperature of 0~5° C. The reaction solution was then stirred overnight at room temperature under the protection of nitrogen gas. The completion of reaction was confirmed by means of the TLC (DCM/EA=1:1). The reaction mixture was poured into iced water, and extracted with EA, and the organic phases were washed with salt solution. The organic phases were combined, subsequently dried and concentrated with anhydrous sodium sulfate, and then purified by silica gel column to obtain 100 mg of compound D.

(4) Preparation of Compound E

The compound D (100 mg, 0.239 mmol) was dissolved in 3 mL of DCM, and trifluoroacetic acid (TFA) (0.5 mL, 6.73 mmol) was added. The reaction solution was stirred at room temperature for 1 hour. The completion of reaction was confirmed by means of the TLC (EA/MeOH=9:1), the reaction product was concentrated by a high-vacuum pump to obtain 220 mg of crude compound E.

(5) Preparation of Compound 4-7

The compound E (220 mg, about 0.239 mmol) was dissolved in 3 mL DMF; the DIPEA (300 mg, 2.320 mmol) and N-Boc-L-tert-leucine (58 mg, 0.251 mmol) were added under protection of nitrogen gas (N$_2$). HATU (110 mg, 0.289 mmol) was then added after the reaction solution was cooled to a temperature of 0~5° C. The reaction solution was stirred overnight at room temperature under the protection of nitrogen gas. The completion of reaction was confirmed by means of TLC (PE/EA=1:1). The reaction mixture was poured into ice water, and extracted with EA, the organic phases were washed with salt solution. The organic phases were combined, and subsequently dried and concentrated with anhydrous sodium sulfate, and then purified by silica gel column to obtain 103 mg of compound 4-7.

(6) Preparation of Compound 4-8

The compound 4-7 (103 mg, 0.194 mmol) was dissolved in 3 mL of DCM, and TFA (0.5 mL, mmol) was added. The reaction solution was stirred at room temperature for 1 hour. The completion of reaction was confirmed by means of TLC (PE/EA=1:1), the reaction product was concentrated by a high vacuum pump to obtain 85 mg of compound 4-8.

(7) Preparation of Compound 4-9

The compound 4-8 (85 mg, 0.194 mmol) was dissolved in 3 mL of DMF; DIPEA (300 mg, 2.320 mmol) and 2,2-dimethyl-4-oxo-3,8,11,14-tetraoxa-5-azahexadecane-16-oleic acid (63 mg, 0.205 mmol) were added under protection of nitrogen gas (N$_2$). HATU (89 mg, 0.234 mmol) was added after the reaction solution was cooled to a temperature of 0~5° C. The reaction solution was then stirred overnight at room temperature under the protection of nitrogen gas. The completion of reaction was confirmed by means of TLC (EA/MeOH=9:1). The reaction mixture was poured into iced water, and extracted with EA, the organic phases were washed with salt solution. The organic phases were combined, and subsequently dried and concentrated with anhydrous sodium sulfate, and then purified with a silica gel column to obtain 75 mg of compound 4-9.

(8) Preparation of Compound 4-10

The compound 4-9 (75 mg, 0.104 mmol) was dissolved in 3 mL of DCM, the EA/HCl (0.5 mL, 2N) were added. The reaction solution was stirred at room temperature for 1 hour. The completion of reaction was confirmed by means of the TLC (EA/MeOH=9:1), the reaction product was concentrated by a high vacuum pump to obtain 103 mg (0.104 mmol) of a compound 4-10.

(9) Preparation of Compound 4-12

The compounds 3-3 (150 mg, 0.394 mmol) and sarcosine (174 mg, 1.953 mmol) were dissolved in 15 mL of DMF, and TEA (400 mg, 3.943 mmol) was added. The reaction solution was then stirred overnight at 90° C. under the protection of nitrogen gas. The completion of reaction was confirmed by means of the TLC (EA/DCM=1:1 and EA/MeOH=9:1). The reaction mixture was poured into ice water, and extracted with EA, the organic phases were washed with salt solution. The organic phases were combined, and subsequently dried and concentrated with anhydrous sodium sulfate. The crude product was purified by silica gel chromatography to obtain a compound 4-12 (63 mg, 0.145 mmol).

(10) Preparation of Compound 4 (Target Compound)

Figure 1:
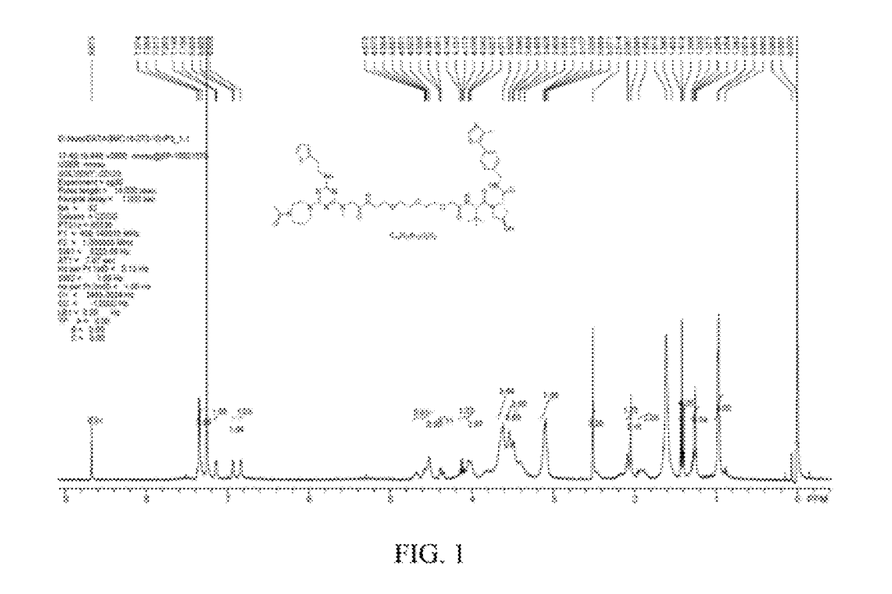
FIG. 1 illustrates a nuclear magnetic resonance spectrogram of a micromolecular compound prepared in Example 1 of the present disclosure.

The compound 4-12 (63 mg, 0.145 mmol) was dissolved in 5 mL DMF; IPEA (200 mg, 1.547 mmol) and compound 4-10 (103 mg, 0.104 mmol) were added under protection of nitrogen gas (N$_2$). HATU (48 mg, 0.236 mmol) was then added after the reaction solution was cooled to a temperature of 0~5° C. The reaction solution was then stirred overnight at room temperature under the protection of nitrogen gas. The completion of reaction was confirmed by means of the TLC (EA/MeOH=9:1). The reaction mixture was poured into iced water, and extracted with EA, the organic phase was washed with salt solution. The organic phases were combined, and subsequently dried and concentrated with anhydrous sodium sulfate, and then purified with a silica gel column to produce 69 mg of compound 4, which was a hygroscopic white foamy solid. The nuclear magnetic resonance spectrogram of the compound was shown in FIG. 1. HPLC purity: 97.8% (254 nm); Mass: M/z 1036 [M+1]$^+$.

Test Example

HEK293 tau cells (stably expressing wild type full length tau protein) is subjected to cell culture and pharmaceutical treatment, and after the HEK293 tau cells were cultured in DMEM medium for 24 hours, the micromolecular compounds prepared in the above example with various concentrations (0 μM, 0.01 μM, 0.1 μM, 1 μM, 10 μM, 20 μM) were added, the cells were further cultured for 24 hours. The cells were lysed with RIPA liquid and the cell extraction solution was collected, the proteins in the cell extraction solution were separated with 10% polyacrylamide gel electrophoresis (PAGE), and subsequently immunoblotted with anti-total tau protein antibody (tau5), and the tau protein content was quantitatively analyzed. The detailed operation procedures for preparation of samples, measurement of protein content in the samples, and the immunoblotting process were performed with reference to the following content.

Preparation of Samples (1) The growth condition and density of cells in the cell culture plates were observed under a microscope;

(2) PBS and cell culture plate were precooled on ice, a mixed liquor consisting of 1× buffer solution+PMSF (1:100)+protease inhibitor cocktail (1:1000) was prepared; 80 μl of the mixed liquor was added into each pore of the 6-well plate, and 150 μl of the mixed liquor was added into a culture dish with a diameter of 6 cm;

(3) The culture medium was sucked by abutting the bottom wall of the cell culture plate with a 1 ml pipette, 1 ml 1×PBS was added by abutting the bottom wall to the cell culture plate, to gently wash the plate 1-3 times according to the cell density; the PBS was sucked with a 1 mL pipette and a 200 μl pipette respectively by abutting the bottom wall of the cell culture plate. After the mixed liquor was added, the cell scraper was washed with ultra-pure water, and the bottom of the pore plate was scratched by the cell scraper a little hard, the cell suspension was sucked out and transferred into 1.5 ml of EP tube, and the cell scrapes shall be washed with ultra-pure water between the operations of different samples;

(4) Boiling was performed for 10 min (initially boiling at the maximum temperature, then maintaining the boiling state at a temperature of 150° C., while the antigen epitope was exposed);

(5) After the centrifugation process, samples were ultrasonicated with 20 kHz ultrasonic pulses for 20 times (in order to open the DNA chains, the ultrasonic machine was switched on and off by pushing the button "I" (switch in) and the button "O" (switch off). When the ultrasonic operation of each sample was performed, the ultrasonic probe was subjected to the ultrasonic operation in double-distilled water for three times, and then wiped and dried with sanitary paper. The ultrasonic probe shall not touch air bubbles and the bottom of the EP-tube);

(6) The samples were oscillated, blended well, and then placed in a refrigerator at −20° C.

II. Measurement of Protein Content in Samples (BCA Method)

(1) The protein samples were oscillated and then diluted appropriately (5 μl of each sample was mixed and diluted with 45 μl of double distilled water, 2 parallel samples were arranged for each sample), and then centrifugated briefly, followed by vibration to mix them well;

(2) Zero μl, 10 μl, 20 μl, 30 μl, 40 μl, 50 μl of 20 mg/ml BSA (100 mg of BSA was dissolved in 5 ml of double distilled water), and 1,000 μl, 990 μl, 980 μl, 970 μl, 960 μl, and 950 μl of double distilled water were respectively added into six standard tubes to prepare the standard protein with a concentration of 0 μg/μl, 0.2 μg/μl, 0.4 μg/μl, 0.6 μg/μl, 0.8 μg/μl and 1.0 μg/μl;

(3) The diluted protein samples and the diluted standard proteins were added separately to 96-well plate (5 μl/pore, PCR pipette was abutting to the interface of the wall and the bottom, pipette tip was replaced after adding the solution into each pore), 3 parallel wells were arranged respectively.

(4) Working solution was prepared by mixing the solution A (personally received) and the solution B (commonly used) in a kit with the ratio of 50:1. The working solution was added into the 96-well plate, 95 μl working solution was added into each pore by means of quick suspension, the lid was used for covering the 96-well plate after completing the filling operation, the 96-well plate was then quickly shaken in the same direction while keeping the working solution at the bottom, the hand was not allowed to touch the bottom of the 96-well plate, the working solution was incubated at 37° C. for 30 min by cushioning the 96-well plate with a plastic box.

(5) The bubble was removed with a 1 ml syringe needle; open the "BioTek" and then "Gen5", click the icon "left arrow" and click the button "OK" and export Excel;

(6) The OD values of standard protein were replicated, the OD values and standard protein concentration were selected to inset a scatter diagram. The data points were selected to add the trend lines, the formula and equation were displayed, the R-squared values were shown (there should be at least two number 9 after the decimal point), and the abnormal values or outliers were removed. The OD values of sample protein were replicated, the corresponding sample group numbers were input at the upper side, the abnormal values or outliers were removed.

III. Measurement of Tau Protein Content (Immunoblotting)

1. A framework was built (two kinds of glass plates, three bottles, five agents, filter paper, sanitary paper, trash can, pipette, gun head, comb were used).

(1) The tabletop and under-frame of the electrophoresis apparatus were wiped cleanly; the comb, glass plate, distilled water bottle, upper and lower gel bottles were washed, the upper and lower gel bottles were dried, the agents for preparing the electrophoresis gel were taken and restored to room temperature.

(2) The upper glass plates were folded inwardly together, the upper portion was pressed such that the lower portion clings to the tabletop and flush with the tabletop, and the clips were clamped outwardly and held glass plates on the underframe.

(3) The double distilled water was injected to check whether the liquid leakage occurred, if so, the framework was rebuilt, the leakage was checked again.

2. Preparation of the electrophoresis gels (see Table 1, the AP and TEMED may be added at 1.5× in cold weather)

TABLE 1

| | Lower part gel (Separating gel) | | Upper part gel (Stacking gel) |
|---|---|---|---|
| | Two pieces of gels | Four pieces of gels | Two pieces of gels |
| 20% Arc/Bis | 4 ml | 6 ml | 1 ml |
| Tris buffer solution | 4 ml (pH = 8.8) | 6 ml (pH = 8.8) | 4 ml (pH = 6.8) |
| 10% AP | 40 μl | 60 μl | 30 μl |
| TEMED | 8 μl | 12 μl | 4 μl |

(1) Twenty percent Arc/Bis, Tris buffer solution, TEMED and 10% AP were sequentially added, the mixture was blown and blended evenly by the pipette, the mixed solution with air bubbles was prevented during the whole process;

(2) The separating gel was slowly injected into the gel film along two corners (when the separating gel was sucked, the pipette was deeply inserted to below the liquid surface, the separating gel was blown and blended evenly, a small amount of liquid was retained at the pipette tip for each suction operation so as to avoid generation of air bubbles), the dosage of each separating gel was 3×900 μl, after observing that the separating gel did not leak, the voids of the gel film were filled with double distilled water along the two corners (so as to prevent oxygen gas from inhibiting polymerization and keep a level of the lower gel, the gel film may be stored for an extended time period);

(3) Wait for about 30 min till the separating gel was coagulated, then the double distilled water was poured out, the remaining water was sucked out with filter paper, and the upper edge of the lower gel was marked with a marking pen;

(4) The stacking gel was slowly injected into the gel film along two corners, the comb with a desired size (a small comb was used when the sample loading amount<20 μl, a large comb was used when the sample loading amount>20 μl) was inserted diagonally from the left to the right, the stacking gel was supplemented between the electrophoresis lanes in order to avoid synaeresis, the gel coagulation process was waited for 50 min.

3. Processing of Samples

After the protein concentration was measured with the BCA method, the bromophenol blue and β-mercaptoethanol (reducing agent) prepared on-site were added according to a ratio between bromophenol blue and β-mercaptoethanol of 1:3, the ratio between the mixed solution and the sample was 1:10, the mixture was subjected to a boiling water bath at 100° C. for 10 min, and then sub-packaged after vibrating in an oscillator for 20 sec; if the result was not desirable, the samples were subjected to a boiling water bath at 100° C. for 10 min before each time of loading the samples.

4. Loading the samples and electrophoretic separating of protein (sample loading pin, samples, comb, Marker, electrophoresis solution, electrophoresis tank, distilled water bottle)

The conductive wire under the electrophoresis frame was washed cleanly, and then transferred to the electrophoresis frame; the lanes were marked and numbered by using a marking pen; the comb was slowly and vertically pulled out, the gel tank was filled with an electrophoresis solution, a trace sample injector was used for sucking samples and adding the samples into lanes (1 μl Marker was loaded in lanes 1 and 8 respectively, the bromophenol blue and 1× Buffer mixed solution were added into the lane 15 to keep equilibration). After loading the samples, the electrophoresis frame was transferred to the electrophoresis tank, the electrophoresis solution was added and a lid was covered on the electrophoresis tank, the red plug (positive electrode of a power supply) was connected with red socket (anode of the electrophoresis instrument), the black plug (negative electrode of a power supply) was connected with the black socket (cathode of the electrophoresis instrument), after the samples were loaded, the electrophoresis process was initially performed with a constant current of 10 mA/block of gel for about 30 min (press twice to start), when the bromophenol blue indicator was running to an interface of the stacking gel and the separating gel and exhibiting a linear shape, the electrophoresis process was altered to a constant pressure of 100V (if the constant pressure was not available, the current was increased) for about 60 min, until the bromophenol blue arrived at the bottom of the gel and the Marker has run off completely.

5. Transferring film (marking NC film, transfer buffer solution, filter paper, ice-box, bowl, tray, transfer film tank, plastic plate, cleaning tweezers)

(1) The NC film marked with a marking pen was dipped into the recycled transfer buffer solution for 10-20 min (in order to facilitate fixation of protein, balance the gel, and remove the SDS), the gel groove was removed by pressing the bayonets at two sides, the middle part at the right side of the glass plate and white ceramic plates was pried up by a small plate, the electrophoresis of the remaining gel was maintained during the process.

(2) Based on the desired molecular weight range to be displayed, the gel was cut vertically slightly inclined with a glass plate and performed mildly at left and right directions back and forth for once, a three-layered filter paper impregnated with the transfer buffer solution was applied on the gel by tweezers, the gel was carefully pried up by a small plate and placed on a sponge (the filter paper was facing down) and the other side was affixed with an inverted NC film, the gel and the NC film were immersed in the transfer buffer solution (the gel was disposed at the upper side), the air bubbles were removed with a glass rod, the gel and the NC film were gripped carefully by tweezers and placed on a hand (the gel was disposed at the upper side), the three-layered filter paper impregnated with the transfer buffer solution was pasted on the gel by tweezers, and placed upside down on a sponge, and a three-layered filter paper was further attached. The following articles were placed from the bottom to the top: a black plastic plate→a layer of sponge→a three-layered filter paper→gel→NC film→a three-layered filter paper→a layer of sponge→a transparent plastic plate, if the articles are loosely disposed, the articles may be fastened with a rubber band.

(3) The red plug (positive electrode of a power supply) was connected with red socket (anode of the electrophoresis instrument), the white plug (negative electrode of a power supply) was connected with the black socket (cathode of the electrophoresis instrument), the transfer buffer tank was placed in an ice bath (the gel shall not be sucked in the transfer buffer solution for a long time before power on, to avoid diffusion and decomposition of protein), the transfer current was the constant current of 276 mA, the voltage was typically about 140V (methyl alcohol may be suitably supplemented to increase the voltage), the specific transfer time was determined according to the molecular weight of the protein to be transferred, the time was 1 h when the molecular weight of the protein to be transferred was less than 100 kDa, and the time was 1.5 h when the molecular weight of the protein to be transferred was more than 100 kDa.

6. Color development of immunoblotting (cleaning tweezers, a box filled with double distilled water, milk, freshness protection package, sanitary paper, primary antibody, ice-box, plate, transparent adhesive tape, TBST, black plastic bag, secondary antibody)

(1) Sealing: after transferring, the NC film was carefully vibrated and sealed with the TBS sealing fluid containing 5% skim milk powder at room temperature for 1 h or at a temperature of 4° C. overnight, and the filter paper without contacting with the gel was recovered.

(2) Incubation of primary antibody: the NC film was taken out, the remaining milk stains on the film surface were rinsed with 1×TBS; the NC film clamped by tweezers stood vertically sanitary paper to remove excess water, and then the NC film was placed in a freshness protection package with the side of Marker outward to remove water and gas with the sanitary paper. The primary antibody (0.1% Tween 20 may be added for lowering the background) was added into the freshness protection package, the freshness protection package was sealed and the seal was pasted on the plate (with Marker and protein upward), the transparent tape shall not be pressed onto the target tape, the freshness protection package was incubated overnight at 4° C.

(3) Incubation of secondary antibody: the NC film was taken out from the incubation bag on the next day and the primary antibody was recycled, the NC film was rinsed with the TBST buffer solution for 3×5 min, the residual salt ions on the film surface were rinsed with 1×TBS, the NC film clamped by tweezers stood vertically sanitary paper to remove excess water, the NC film was placed in a freshness protection package to remove water and gas with the sanitary paper. The fluorescein-labeled goat anti-rabbit or goat anti-mouse Odyssey secondary antibody (0.1% Tween 20 may be added for lowering the background) was added into the freshness protection package in a dark place, the freshness protection package was sealed and the seal was pasted on the plate (with Marker and protein upward), the transparent tape shall not be pressed onto the target tape, after slowly shaking the package and incubating at room temperature for 1 h (the incubation time over 1 h may increase background, the incubation time may extend to 2 h in cold weather), the NC film was taken out from the incubation bag and the secondary antibody was recycled, the NC film was rinsed with TBST buffer solution for 3×5 min. After completion of the rinsing process, the residual salt ions on the film surface were rinsed with 1×TBS.

(4) Color development: the glass plate was initially wiped clean with a lens wiping paper dipped with anhydrous ethanol. The Marker side was placed downward, the NC film was placed on the scanner from top to bottom with the molecular weight of samples from small to large, and covered with a plastic film; air was exhausted. Open the Odyssey software, click "File"→"New"→"Browse"→input date, click "Obtain image" to select the length and width of the sweeping film, scan the images and save the original drawing, click the "Alter image" to adjust the images, mark the samples and antibody types with text box, click "Export image File"→"Save", the film was collected and the glass plate was wiped cleanly with sanitary paper.

Figure 2:
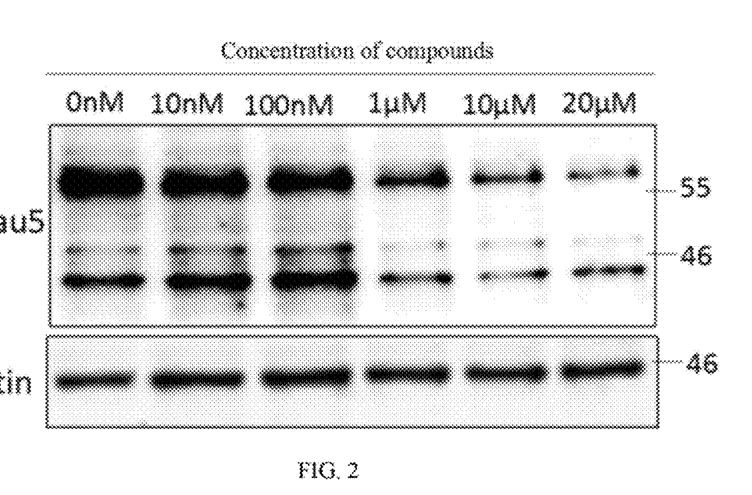
FIG. 2 illustrates a photograph comparing the degradation results of tau protein using the micromolecular compound of the present disclosure with different concentrations.
Figure 3:
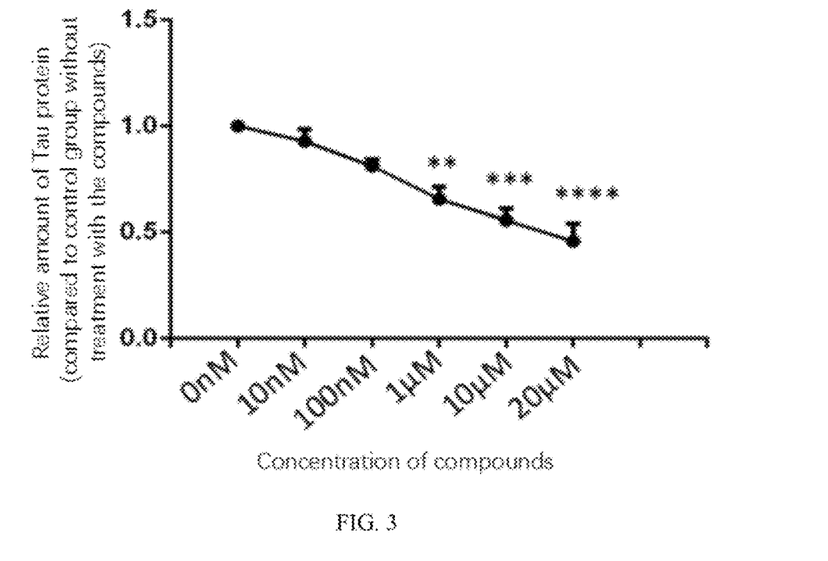
FIG. 3 illustrates a quantitative analysis graph showing the degradation results of tau protein using the micromolecular compound of the present disclosure with different concentrations.
Figure 4:
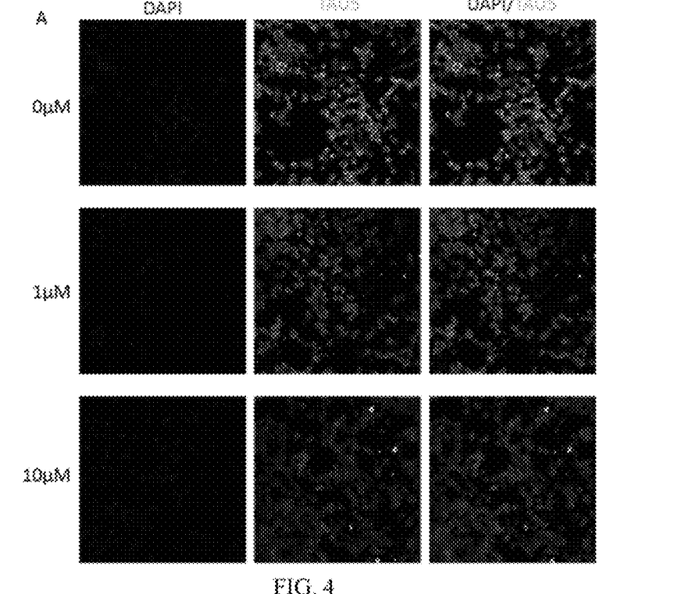
FIG. 4 illustrates a fluorescence photograph of the micromolecular compound of the present disclosure for reducing total tau protein content in the HEK293 tau cells.

FIG. 2 illustrates a photograph comparing the degradation results of tau protein using the micromolecular compound in the test example of the present disclosure with different concentrations. FIG. 3 illustrates a quantitative analysis graph showing the degradation results of tau protein using the micromolecular compound in the test example of the present disclosure with different concentrations. The results show that 1 μM, 10 μM, and 20 μM of compounds can dose-dependently reduce the content of tau protein in cells. FIG. 4 illustrates a fluorescence photograph of the micromolecular compound with different concentrations of the present disclosure for reducing total tau protein content in the HEK293 tau cells.

As can be seen, the micromolecular compound specifically degrading tau protein of the present disclosure can reduce the content of tau protein in cells. Because the abnormal aggregation of tau protein within cells is associated with more than 20 neurodegenerative diseases, the aggregation amount of tau protein is positively correlated with neurodegeneration and memory impairment in degenerative diseases, as a result, the degradation of tau protein can lead to prevention or/and treatment of tau-associated neurodegenerative disorders, such as Alzheimer's disease, frontotemporal dementia linked to chromosome-17 with Parkinsonism, Pick's disease, progressive supranuclear palsy, corticobasal degeneration, primary age-related tauopathy, argyrophilic grain disease, age-related tauopathy, chronic traumatic encephalopathy, globular glial tauopathy, Parkinson's disease, Huntington's disease, cerebral stroke, and epilepsy.

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

The invention claimed is:

1. A micromolecular compound specifically degrading tau protein, wherein the chemical structure of the compound is TBM-L-ULM, or a pharmaceutically acceptable salt, enantiomer, stereoisomer, solvate, polymorph, or N-oxide thereof, wherein TBM is tau protein binding moiety, L is a linker group, and ULM is a ubiquitin ligase binding moiety, the tau protein binding moiety is connected with the ubiquitin ligase binding moiety via the linker group;

wherein the TBM is a group having the structure expressed by Formula (2), or a group further modified by a substituent at the sites ①, ②, ③, ④, ⑤, ⑥, ⑦, ⑧, ⑨ or ⑩ of a group having the structure expressed by Formula (2), wherein TBM is connected with the linker group L through sites ①, ②, ③, ④, ⑤, ⑥, ⑦, ⑧, ⑨ or ⑩ of Formula (2), Formula (2)

Wherein $R^{14}$ is a C1-C4 alkylene, $R^{15}$ and $R^{16}$ each is a C1-C4 alkyl, $R^{17}$ is a bond, H, a C1-C4 alkyl, or —$R^{18}$—C(O)—, wherein $R^{18}$ is a C1-C4 alkylene.

2. The micromolecular compound of claim 1, wherein ULM is capable of binding with E3 ubiquitin ligase.

3. The micromolecular compound of claim 2, wherein the E3 ubiquitin ligase is VHL E3 ubiquitin ligase or CRBN E3 ubiquitin ligase.

4. The micromolecular compound of claim 1, wherein ULM is a group having a structure represented by Formula (1),

Formula (1)

wherein $E^1$ is O, S, $CHR^{12}$ or $NR^{12}$, $R^{12}$ is H or a C1-C3 alkyl optionally substituted with one or two hydroxyl groups;

Z is -A—B—, wherein A is a bond, O, or S; B is a bond, a C1-C4 alkylene, or —$R^{13}$—C(O)—, wherein $R^{13}$ is a C1-C4 alkylene.

6. The micromolecular compound of claim 1, wherein the structural formula of the micromolecular compound is:

Wherein $R^1$ is a hydroxyl, or a group which is metabolized to a hydroxyl in the body of a patient or a subject;

$R^2$ is —NH—$R^4$—Ar-HET, wherein $R^4$ is a C1-C3 alkylene, Ar is a C6-C12 arylene, and HET is an optionally substituted thiazole or isothiazole;

$R^3$ is —$CHR^5$-M-, the ULM is connected with the linker group L via M, wherein $R^5$ is a C1-C4 alkyl, M is a bond, a C1-C4 alkylene, —NH— or —NH—C(O)—$R^6$—, wherein $R^6$ is a C1-C4 alkylene.

5. The micromolecular compound of claim 1, wherein L is the group —X—Y—Z—, X is linked to TBM, and Z is linked to ULM, wherein X is a bond, C1-C4 alkylene, —NH— or —NH—C(O)—$R^7$—, wherein $R^7$ is a bond or a C1-C4 alkylene;

Y is —$R^8$—($R^{10}$-E—$R^{11}$)$_n$—$R^9$—, wherein $R^8$ and $R^9$ each is a bond or a C1-C8 alkylene, $R^{10}$ and $R^{11}$ each is a C1-C4 alkylene, n is an integer of 0-10, E is O, S, an amide group, a piperazinyl group, $NR^{12}$, S(O), $S(O)_2$, —$S(O)_2O$, —$OS(O)_2$, $OS(O)_2O$, or 7. The micromolecular compound of claim 2, wherein the ULM is a group having a structure represented by Formula (1), Formula (1)

Wherein $R^1$ is a hydroxyl, or a group which is metabolized to a hydroxyl in the body of a patient or a subject;

$R^2$ is —NH—$R^4$—Ar-HET, wherein $R^4$ is a C1-C3 alkylene, Ar is a C6-C12 arylene, and HET is an optionally substituted thiazole or isothiazole;

$R^3$ is —$CHR^5$-M-, the ULM is connected with the linker group L via M, wherein $R^5$ is a C1-C4 alkyl, M is a bond, a C1-C4 alkylene, —NH— or —NH—C(O)—$R^6$—, wherein $R^6$ is a C1-C4 alkylene.

8. The micromolecular compound of claim 3, wherein the ULM is a group having a structure represented by Formula (1), Formula (1)

Wherein R¹ is a hydroxyl, or a group which is metabolized to a hydroxyl in the body of a patient or a subject;

R² is —NH—R⁴—Ar-HET, wherein R⁴ is a C1-C3 alkylene, Ar is a C6-C12 arylene, and HET is an optionally substituted thiazole or isothiazole;

R³ is —CHR⁵-M-, the ULM is connected with the linker group L via M, wherein R⁵ is a C1-C4 alkyl, M is a bond, a C1-C4 alkylene, —NH— or —NH—C(O)—R⁶—, wherein R⁶ is a C1-C4 alkylene.

9. A method for degrading tau protein in a patient body in need, wherein the method comprises administering the patient with an effective amount of the micromolecular compound of claim 1.

10. The method of claim 9, wherein the micromolecular compound is administered to the patient by at least one mode selected from the group consisting of: nasal, inhalation, topical, oral, intramuscular, subcutaneous, transdermal, peritoneal, epidural, intrathecal and intravenous routes.

\* \* \* \* \*